United States Patent [19]

Udovich et al.

[11] Patent Number: 4,482,726
[45] Date of Patent: Nov. 13, 1984

[54] PROCESS FOR THE PRODUCTION OF MALEIC ANHYDRIDE

[75] Inventors: Carl A. Udovich, Joliet; William S. Eryman, Bolingbrook, both of Ill.

[73] Assignee: Standard Oil Company (Indiana), Chicago, Ill.

[21] Appl. No.: 509,151

[22] Filed: Jun. 28, 1983

Related U.S. Application Data

[62] Division of Ser. No. 382,182, May 26, 1982, Pat. No. 4,418,003.

[51] Int. Cl.$^3$ ............................................ C07D 307/60
[52] U.S. Cl. ...................................... 549/260; 549/259
[58] Field of Search ................................ 549/259, 260

[56] References Cited

U.S. PATENT DOCUMENTS 3,864,280  2/1975  Schneider ........................... 252/435
3,985,775  10/1976  Harrison ........................... 252/437 X
4,283,288  8/1981  Udovich et al. ..................... 252/437

Primary Examiner—John M. Ford
Assistant Examiner—Bernard I. Dentz
Attorney, Agent, or Firm—Gunar J. Blumberg; William T. McClain; William H. Magidson

[57] ABSTRACT

A novel catalyst for the oxidation of butane to produce maleic anhydride comprising a phosphorus and vanadium mixed oxide wherein the catalyst is prepared by using $P_2O_5$ in an organic medium wherein the catalyst is not precipitated. The catalyst has a specific phase identified by a characteristic X-ray diffraction pattern. A process for the manufacture of the catalyst and a process for the manufacture of maleic anhydride from butane feedstock utilizing the novel catalyst is disclosed. Maleic anhydride is a well-known industrial chemical used in the manufacture of polyester, and maleic anhydride also has utility as a food stuff.

12 Claims, No Drawings

PROCESS FOR THE PRODUCTION OF MALEIC ANHYDRIDE

This is a division of application Ser. No. 382,182 filed May 26, 1982 now U.S. Pat. No. 4,418,003.

BACKGROUND OF THE INVENTION

1. Field of the Invention

The field of this invention relates to the production of maleic anhydride from n-butane and to a novel process for the manufacture of novel catalysts for the manufacture of maleic anhydride.

2. Background

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butene is well known and until recently the principal method employed for the manufacture of maleic anhydride was by the air oxidation of benzene in the presence of certain heavy metal oxide catalysts. However, because of the inherent toxicity of benzene fumes, the trend has been to eliminate the utilization of benzene as a feedstock and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339 and British Pat. application No. 2,019,839A. While the aforementioned prior art tends to bring about some improvement in the performance of the phosphorus vanadium catalyst there remains much room for improvement, particularly from the standpoint of high conversion, yield and catalyst life.

The object of the present invention is to provide a phosphorus vanadium oxide catalyst or advantageously a phosphorus vanadium metal mixed oxide catalyst wherein the metal has a valence of at least two and is prepared in an organic medium. Prior to its use in the manufacture of maleic anhydride from butane feedstock the mixed oxide is in a phase comprising in excess of 50 percent of a characteristic powder X-ray diffraction pattern using copper K-alpha radiation as follows:

| d angstrom | Line Position 2.0 degrees | Intensity |
|---|---|---|
| 8.75 | 10.1 | 38 |
| 5.7 | 15.2 | 23 |
| 4.5 | 19.4 | 24 |
| 3.7 | 24.0 | 31 |
| 3.3 | 26.8 | 32 |
| 3.1 | 28.3 | 24 |

-continued

| d angstrom | Line Position 2.0 degrees | Intensity |
|---|---|---|
| 2.9 | 30.3 | 100 |

Another object is to provide a process for the manufacture of phosphorus vanadium catalysts including phosphorus vanadium catalysts having metal activators. A further object is to provide a process for the manufacture of maleic anhydride from butane at a temperature of about 650° to about 850° F. in the presence of the novel catalyst.

The novel catalyst comprises a phosphorus vanadium metal oxide or alternatively a phosphorus vanadium mixed oxide promoted by a metal. Preferred metals have been found to be zinc or molybdenum. The atomic ratio of the vanadium to phosphorus can suitably be in the range of 0.5:1.0 to 1.25:1.0, preferably in the range of 0.6:1.0 to 1.0:1.0. The total atomic ratio of zinc or molybdenum to vanadium advantageously is in the range of 0.005:1 to 0.4:1. It is preferred that the total atomic ratio of zinc or molybdenum to vanadium should be in the range of 0.01:1 to 0.25:1. The atomic ratio of phosphorus to vanadium is suitably in the range of 0.8:1 to 2:1, preferably 1:1 to 1.7:1.

Our novel catalyst is prepared from an alcoholic solution which has been reacted with phosphorus pentoxide and has then been saturated with an acid, suitably gaseous hydrogen chloride. Preferred alcohols are methanol and ethanol. The acidified alcoholic solution serves both as a reducing agent and solvent in our novel process for the manufacture of phosphorus vanadium catalysts. Our catalyst preparation proceeds according to the following reaction sequence:

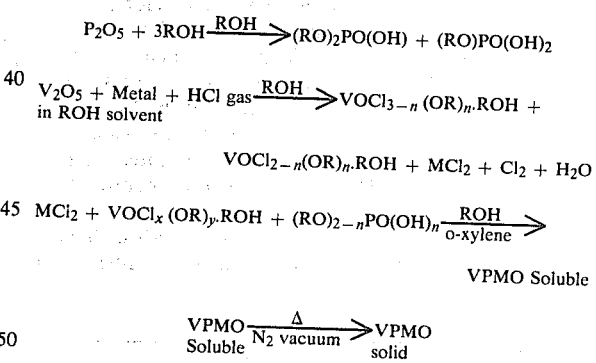

In the foregoing reaction scheme x, y, m, n are integers. M is a metal, preferably zinc or molybdenum, but no metal need be present. The foregoing is representative of the formation of a mixed metal oxide. The acidified alcohol solution provides a solvent system in which the catalyst system is soluble. In our process for the manufacture of the catalyst, the catalyst does not precipitate from the reaction media. The use of $P_2O_5$ is a critical feature of our invention, enabling mixed acid phosphate esters to be formed which are advantageously incorporated within the catalyst precursors. This results in the formation of a unique active catalyst suitable for the oxidation of butane to maleic anhydride with high selectivity and yield. The final catalyst is advantageously obtained in a quantitative amount by evaporation of the solvent after a suitable period of catalyst development reflux time. The use of phosphorus pentoxide has a further advantage over 100 percent crystalline phosphoric acid in that it is commercially available at reasonable cost. This is not the case with 100 percent crystalline phosphoric acid, which can only be obtained from laboratories selling specialty chemicals. Our catalysts also show much higher activity than catalysts of the prior art provided by an aqueous base route such as is disclosed in U.S. Pat. Nos. 3,862,146, and 4,328,126.

In our process, monovalent metals such as sodium and lithium cannot be used efficiently. They tend to deactivate our catalyst. Suitably, organic solvents for our catalyst are alcohols or mixtures of alcohols with aromatic hydrocarbons such as ortho-xylene. Aliphatic alcohols are usually employed in the process and methanol is the preferred alcohol. The metal such as zinc or molybdenum may be added as a compound together with vanadium or separately introduced into the solution. Suitable zinc or molybdenum compounds comprise metallic zinc, or molybdenum chloride, zinc chloride, or molybdenum oxychloride, zinc oxide or molybdenum oxide, and most soluble zinc or molybdenum salts. If it is desired to improve physical properties of the catalysts, they may be treated with the suspension of an inert support; for example, alumina, titania, silicon carbide, kieselguhr, pumice or preferably, silicon. The catalyst may be reinforced with such materials at any stage in its preparation.

Other useful metals include zirconium, niobium, cerium, chromium, manganese, nickel and uranium.

According to our process, the average valence of vanadium is in the range of about 3.8 to 4.2. The vanadium compound can be vanadium pentoxide, vanadium tetrachloride, vanadium trichloride, vanadium oxydichloride, vanadium oxytrichloride, vanadium tetroxide, vanadium oxalate, and most soluble vanadium complexes. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium containing acids such as metavanadic acid, pyrovanadic acid and the like; vanadium salts such as ammonium metavanadate, vanadium sulfate, vanadium phosphate, vanadyl formate, vanadyl oxalate and the like. However, vanadium pentoxide is preferred.

It has been discovered that the novel catalysts have a characteristic phase one showing an X-ray diffraction pattern as follows:

| d angstrom | Line Position 2.0 degrees | Intensity |
|---|---|---|
| 8.75 | 10.1 | 38 |
| 5.7 | 15.2 | 23 |
| 4.5 | 19.4 | 24 |
| 3.7 | 24.0 | 31 |
| 3.3 | 26.8 | 32 |
| 3.1 | 28.3 | 24 |
| 2.9 | 30.3 | 100 |

The aforementioned X-ray form comprises at least 50 percent of the catalyst. This catalyst shows excellent selectivity and yield in the manufacture of maleic anhydride from butane. Also, this catalyst has a long life and can be regenerated in situ, thus, making it useful for the commercial production of maleic anhydride.

In a preferred embodiment, our novel catalyst is produced by generating a vanadium species, V(IV), in situ by the reduction of $V_2O_5$ with acidified methanol in the presence of a second cometal such as zinc or molybdenum and subsequently reacting the catalyst with mixed phosphate acid esters generated in situ. Our process is quantitative and recovers 100 percent of the vanadium feedstock compared to the precipitative technique of the prior art, which recovers only about 60 percent of the vanadium. In our process no precautions are taken to remove water during the reaction to ensure a completely anhydrous nature and ortho-xylene is used as an example of a conditioning agent.

The catalyst prepared according to the preferred embodiment has a P/V ratio of about 1.2:1 to 1.3:1. Among the many advantages of our novel catalyst manufacturing process can be cited the quantitative use of vanadium, the use of the inexpensive $P_2O_5$ and the use of inexpensive alcohols such as methanol. As a further refinement of our process for the manufacture of our novel catalyst, the $P_2O_5$ addition can advantageously be carried out in two stages. This refinement can suitably be carried out by carrying out a major addition right after reduction of the vanadium pentoxide and carrying out a second addition to a concentrated syrup of a preliminarily formed P/V mixed oxide or a P/V/Zn mixed oxide or a P/V/Mo mixed oxide. The advantage of this improved process is that the catalyst so formed is more active and thus, useful in the manufacture of the maleic anhydride by the oxidation of butane at lower temperatures. This catalyst is also much more selective than conventionally formed catalysts from either an aqueous based quantitative formulation such as disclosed in U.S. Pat. Nos. 3,862,146 and 4,328,126, or from precipitative techniques which are employed by the prior art reference cited herein. These catalysts operate at lower temperatures which should enable them to have a much longer life than those which must be operated at 50° or 100° F. higher.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic manufactures of oxygen and diluent gases such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4000 cc of feed per cc of catalyst per hour and more preferably about 1000 to 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury and at 25° C. A variety of reactors will be found to be useful and multiple tube heat exchanger type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at relatively constant temperatures and some medium to conduct heat from the reactors is necessary to aid temperature control. Such media may be Woods metal, molten sulphur, mercury, molten lead and the like, but it has been found that eutectic salt baths are completely satisfactory. One such salt bath is a sodium nitrate, sodium nitrite-potassium nitrate eutectic constant temperature mixture. An additional method of temperature control is to use a metal block reactor whereby the metal surrounding the tube acts as a temperature regulating body. As will be recognized by a man skilled in the art, the heat exchanger medium may be kept at the proper temperature by heat exchangers and the like. The reactor or reaction tubes may be iron, stainless steel, carbon steel, nickel, glass tubes such as vycor and the like. Both carbon steel and nickel tubes have excellent long life under the conditions of the reaction described herein. Normally, the reactors contain a preheat zone under an inert material such as one-quarter inch alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

The reaction may be conducted at atmospheric, superatmospheric, or below atmospheric pressure. The exit pressure will be at least slightly higher than the ambient pressure to ensure a positive flow from the reactor. The pressure of the inert gases must be sufficiently high to overcome the pressure drop through the reactor.

Maleic anhydride may be recovered by a number of ways well known to those skilled in the art. For example, the recovery may be by direct condensation or by absorption in suitable media, with specific operations and purification of the maleic anhydride. The following examples will serve to provide a fuller understanding of the invention, but it is to be understood that these examples are given for illustrative purposes only and will not be interpreted as limiting the invention in any way. In the examples the terms "conversion", "selectivity" and "yield" are defined as follows:

$$\text{Conversion \%} = \frac{\text{Moles hydrocarbon reacted}}{\text{Moles hydrocarbon in feed}} \times 100$$

$$\text{Selectivity \%} = \frac{\text{Moles maleic produced}}{\text{Moles hydrocarbon feed consumed}} \times 100$$

$$\text{Yield Wt. \%} = (\text{Conversion}) \times (\text{Selectivity}) \times 169$$

EXAMPLE 1

To a 2-liter 4-neck flask equipped with mechanical stirrer, reflux condenser, thermometer, submersible gas inlet tube, and capable of being heated by an electric mantle are charged 500 ml of methanol and 92 g (0.65 m) of granular phosphorus pentoxide (in 3–5 increments). The phosphorus pentoxide is allowed to react with the methanol under rapid mechanical agitation with external cooling of the reactor with an ice-water bath. The temperature is maintained at less than 50° C. After the $P_2O_5$ has reacted/dissolved, 91 g (0.5 m) of vanadium pentoxide, $V_2O_5$, and 4.4 g of molybdenum trioxide are added to the solution. Gaseous hydrogen chloride is introduced by means of the submerged dip leg at such a rate as not to be detected at the condenser outlet. The solution warms during the addition of the hydrogen chloride but is maintained at less than 50° C. by external cooling of the reactor. The solution becomes homogeneous redbrown in color without any apparent suspended solids present. At this stage, the vanadium exists as a mixture of +4 and +5 oxidation states and molybdenum is in the +6 oxidation state. An additional 75 ml of methanol are added along with 200 ml of o-xylene and the solution is brought to reflux and allowed to reflux 18 hours while being stirred. The solution is deep blue in color at this stage and no solids are evident. The solvent volume is reduced by side arm distillation to about 150–200 mls and the solution poured into a teflon dish. The solution is dried in a vacuum oven at 20 inches Hg vacuum under a nitrogen bleed at 220°–350° F. overnight. The dried cake developed a brown amorphous dome of material (1–3 weight percent) over a deep blue solid bottom. The components were mechanically separated.

EXAMPLE 2

The catalyst prepared in Example 1 was combined with 5 weight percent of graphite and tableted as cored 3/16" pills. A 6 cc loading of catalyst was placed in a minireactor under a 1.05 percent butane-synthetic air mixture and the temperature raised to 665° F. over a 4–6 hour time period. The temperature was raised to 788° F. after 24 hours. The catalyst was then evaluated at various temperatures at the equivalence of 1200–1300 volume hourly space velocity, VHSV, and the results are given in Table I hereinbelow. The performance of this catalyst indicates a yield increase to 90 weight percent with excellent selectivity of 65–66 mole percent. It is anticipated that yields will increase with time on stream.

TABLE I

| # of Pills | 34 | | |
|---|---|---|---|
| Wt. of Pills | 4.37 g | | |
| Vol. | 6 cc | Flow 120 cc/MIN | $P_2O_5/CH_3OH;Mo$ |
| Time on Stream (Days) | | Temp. °F. | Conversion (mole %) |
| | | Brought up to 500° F. held 30 min., Brought up to 650° F. 665° | |
| | | — | Raised temp. to 785° F. |
| 2 | | 788 | 18.19 |
| 5 | | 811 | 72.46 |
| 6 | | 811 | 74.71 |
| 7 | | 812 | 74.97 |
| 8 | | 811 | 73.08 |
| 9 | | 812 | 74.30 |
| 12 | | 812 | 78.41 |

TABLE I-continued

| | | |
|---|---|---|
| 13 | 818 | 78.70 |
| 14 | 819 | 78.78 |
| 16 | 819 | 80.00 |
| 19 | 818 | 80.10 |
| 20 | 818 | 81.01 |
| 21 | 818 | 80.74 |
| 22 | 818 | 80.72 |

| Selectivity (mole %) | Yield (weight %) | $CO/CO_2$ Ratio |
|---|---|---|
| 48.23 | 14.80 | 2.09 |
| 62.56 | 76.48 | 1.76 |
| 64.08 | 80.76 | 1.76 |
| 66.02 | 83.51 | 1.71 |
| 65.64 | 80.93 | 1.78 |
| 65.62 | 82.25 | 1.75 |
| 64.45 | 85.25 | 1.75 |
| 65.01 | 86.31 | 1.75 |
| 65.11 | 86.53 | 1.73 |
| 65.39 | 88.26 | 1.71 |
| 65.54 | 88.56 | 1.68 |
| 65.81 | 89.94 | 1.70 |
| 65.40 | 89.07 | 1.67 |
| 65.13 | 88.69 | 1.70 |

EXAMPLE 3

To the same type of reactor as described in Example 1, 500 ml of methanol, 71 g of $P_2O_5$, 4.4 g of molybdenum trioxide and 91 g (0.5 m) of vanadium pentoxide were added. Gaseous hydrogen chloride was added in a similar fashion. The solution was reduced in volume by side arm distillation to approximately 225 ml and an additional 18 g (0.126 m) of phosphorus pentoxide were added to the reduced volume syrup. The mixture was heated and stirred an additional 30 minutes to take the added $P_2O_5$ into solution. The solution was poured into a teflon dish and dried in a vacuum oven at 20 inches Hg vacuum under a nitrogen bleed at 220°–350° F. overnight.

EXAMPLE 4

The catalyst prepared in Example 3 was combined with 5 weight percent graphite and tableted as cored 3/16" pills at 10 pounds crush strength. A 6 cc loading of catalyst was placed in a minireactor under a 1.05 percent butane-synthetic air mixture and the temperature was raised to 760° F. within 6 hours. The catalyst was evaluated at various temperatures at the equivalence of 1200–1300 $hr^{-1}$ volume hourly space velocity, VHSV, and the results are given in Table II hereinbelow. The performance of this catalyst which continued to activate after 41 days on stream and 780° F. was CSY (conversion, selectivity and yield) of 86/67/97 weight percent. This is judged as an excellent performance for a maleic anhydride catalyst under these conditions.

TABLE II

Wt = 4.9/g
Vol = 6.00 cc
Pills = 38.0

| Time on Stream (Days) | Temp. °F. | $P_2O_5/P_2O_5$ in syrup Conversion (mole %) |
|---|---|---|
| 1 | 760 | 23.95 |
| 5 | 780 | 59.93 |
| 8 | 813 | 80.51 |
| 9 | 812 | 80.56 |
| 12 | 812 | 80.89 |
| 14 | 812 | 83.54 |
| 15 | 813 | 81.01 |
| 16 | 813 | 85.38 |
| 19 | 813 | 79.79 |
| 19 | 812 | 82.89 |
| 21 | 812 | 82.77 |
| 25 | 812 | 85.57 |
| 27 | 812 | 85.67 |
| 29 | 811 | 86.04 |
| 32 | 819 | 91.64 |
| 33 | 806 | 89.61 |
| 34 | 790 | 84.82 |
| 35 | 790 | 84.23 |
| 36 | 790 | 85.36 |
| 39 | 779 | 84.42 |
| 41 | 780 | 85.64 |

| Selectivity (mole %) | Yield (weight %) | $CO/CO_2$ |
|---|---|---|
| 71.51 | 28.89 | 1.93 |
| 65.18 | 65.90 | 1.79 |
| 62.83 | 85.33 | 1.87 |
| 61.65 | 83.78 | 1.70 |
| 63.89 | 87.19 | 1.73 |
| 63.62 | 89.66 | 1.72 |
| 64.46 | 88.09 | 1.73 |
| 64.35 | 92.70 | 1.72 |
| 65.30 | 87.89 | 1.70 |
| 65.15 | 91.11 | 1.66 |
| 64.84 | 90.54 | 1.67 |
| 64.07 | 92.50 | 1.67 |
| 63.48 | 92.07 | 1.61 |
| 64.11 | 93.05 | 1.62 |
| 62.06 | 95.94 | 1.59 |
| 63.26 | 95.64 | 1.61 |
| 66.50 | 95.16 | 1.52 |
| 67.33 | 95.67 | 1.58 |
| 65.52 | 94.35 | 1.58 |
| 67.47 | 96.08 | 1.51 |
| 66.86 | 96.59 | 1.57 |

EXAMPLE 5

To the same reactor setup as described in Example 1 were added 500 ml of methanol, 91 g (0.5 m) of vanadium pentoxide and 4.4 g of molybdenum trioxide. The vanadium pentoxide was reduced with gaseous hydrogen chloride in the same manner. After reduction, 168 g (1.2 m) of trimethylphosphate, $(CH_3O)_3PO$ and 200 ml of o-xylene were added. The solution was refluxed for 18 hours and was then reduced in volume to about 200–250 mls. The syrup was deep blue in color, the same color as in Examples 1 and 3. The syrup was poured into a teflon dish and dried as shown in the previous examples in a vacuum oven overnight. The material became brown and amorphous in nature similar to the dome material in Example 1. This material could not be tableted.

EXAMPLE 6

Triethylphosphate $(EtO)_3PO$, and tributylphosphate, $(BuO)_3PO$ were similarly tried as in Example 5. The dried material was a brown amorphous composition which could not be tableted.

EXAMPLE 7

Thirty-four grams of phosphorus pentoxide was slowly added to 100 cc of methanol with rapid agitation. No special precautions were taken to ensure anhydrous conditions or water uptake under experimental conditions. The sample was cooled and the $p^{31}$ nmr was run on it at room temperature. The sample was found to contain 55 percent $(CH_3O)PO(OH)_2$, 36 percent $(CH_3O)_2PO(OH)$, 2 percent $(CH_3O)_3PO$ and the remainder was $H_3PO_4$.

EXAMPLE 8

A 100 ml sample of methanol was saturated with gaseous hydrogen chloride and then twenty grams (20 g) of phosphorus pentoxide was added. The solution was refluxed twenty minutes, cooled and submitted for analyses by $p^{31}$ nmr. The sample was found to contain 56 percent $(CH_3O)PO(OH)_2$, 34 percent $(CH_3O)_2PO(OH)$, 1 percent $(CH_3O)_3PO$ and the remainder $H_3PO_4$.

EXAMPLE 9

To a 2-liter, 4-neck flask equipped with mechanical stirrer, reflux condenser, thermometer, submersible gas inlet tube and electric heating mantle, 500 ml of methanol were charged. To the alcohol, 85.2 grams of phosphorus pentoxide, $P_2O_5$, was added in increments to control the temperature. Once the $P_2O_5$ had reacted/dissolved, 91 g of vanadium pentoxide, $V_2O_5$, and 11.7 g of zinc metal, Zn, were added. The vanadium pentoxide was then reduced while the zinc was oxidized by gaseous HCl which was introduced through the dip leg. The solution became homogeneous and uniform in color without suspended solids. Two hundred mls of o-xylene were added and the mixture was then refluxed for 12-18 hrs. The solvent was then removed to the point where a viscous but pourable syrup remained. This syrup was transferred to a teflon evaporation dish and dried at 118° C. under 3 inches of mercury vacuum.

EXAMPLE 10

The dried catalyst of Example 9 was blended with 5 weight percent Sterotex and tableted as 3/16" hollow core tablets. A 6 cc loading of catalyst was evaluated in a minireactor under a 1.05 percent butane-synthetic air mixture and the temperature was raised to 600° F. over a 4-6 hour period. The catalyst was then evaluated at various temperatures at the equivalence of about 1200-1300 volume hourly space velocity, VHSV, and the results are given below:

| Time on Stream (Days) | Temperature (°F.) | Conversion (mole %) | Selectivity (mole %) | Yield (wt %) |
|---|---|---|---|---|
| 1 | 759 | 82 | 62 | 86 |
| 8 | 759 | 73 | 69 | 85 |
| 19 | 771 | 71 | 72 | 86 |

EXAMPLE 11

To the same type of reactor as described in Example 9 were added 500 ml of methanol, 91 g (0.5 gfw) $V_2O_5$, and 11.77 g (0.18 gaw) of zinc. Gaseous hydrogen chloride was added in a similar fashion until the solution was homogeneous without suspended solids. To the solution was added 71 g (0.5 gaw) of $P_2O_5$ and 200 ml of o-xylene. The solution was refluxed for about 12-18 hours and then the volume was reduced by side arm distillation to about one-third the original level. An additional 14.2 g (0.1 gfw) of $P_2O_5$ were added and the solution was refluxed an additional hour. Additional solvent was removed until a pourable but viscous syrup remained. This syrup was transferred to a teflon dish and dried in a vacuum oven at 110° C. to form a pale blue solid.

EXAMPLE 12

The dried catalyst of Example 11 was blended with 5 weight percent Sterotex and tableted as 3/16" cored tablets. A 6 cc loading was treated as in Example 10. The catalyst was evaluated at various temperatures and space velocities and the results are given below:

| Time on Stream (Days) | Volume Space Velocity (hr$^{-1}$) | Temperature (°F.) | Conversion (mole %) | Selectivity (mole %) | Yield (weight %) |
|---|---|---|---|---|---|
| 1 | 1200 | 760 | 88 | 55 | 82 |
| 2 | 1400 | 752 | 87 | 62 | 90 |
| 16 | 1800 | 769 | 72 | 69 | 84 |

EXAMPLE 13

To the same type of reactor as described in Example 9 were added 750 ml of methanol, 91 g (0.5 gfw) $V_2O_5$ and 6.5 g (0.1 gaw) of zinc. Gaseous hydrogen chloride was introduced at such a rate as not to be detected at the condenser outlet. After the solution becomes homogeneous without suspended solids, 125 g of crystalline orthophosphoric acid were added in an additional 100 ml of methanol. One hundred mls of benzene was added followed by an additional 150 ml within one hour. The solution was refluxed overnight. The solution was concentrated and the solids precipitated. The blue solids were filtered, washed with methanol and dried in a vacuum oven at 107° C. The powder was combined with 5 weight percent Sterotex and tableted. A minireactor evaluation of 1200 volume hourly space velocity is given below: (comparison example using crystalline orthophosphoric acid)

| Time on Stream (Days) | Temperature (°F.) | Conversion (mole %) | Selectivity (mole %) | Yield (weight %) |
|---|---|---|---|---|
| 1 | 802 | 86 | 53 | 77 |
| 7 | 802 | 84 | 61 | 86 |
| 29 | 803 | 81 | 61 | 83 |

EXAMPLE 14

The same means as described in Example 13, a catalyst was prepared without the use of a co-metal. The results of that catalyst are shown as below:

| Time on Stream (Days) | Temperature (°F.) | Conversion (mole %) |
|---|---|---|
| 35 | 789 | 80 |

| Selectivity (mole %) | Yield (weight %) | Volume Hourly Space Velocity (hr$^{-1}$) |
|---|---|---|
| 54 | 74 | 1200 |

Catalyst to which zinc has been added as shown in Example 13 have the following values:

| Time on Stream (Days) | Temperature (°F.) | Conversion (mole %) |
|---|---|---|
| 35 | 774 | 74 |

| Selectivity (mole %) | Yield (weight %) | Volume Hourly Space Velocity (hr$^{-1}$) |
|---|---|---|

-continued

| 67 | 84 | 1710 |

We claim:

1. A process for the manufacture of maleic anhydride which process comprises contacting a feedstock comprising n-butane and a gas containing molecular oxygen in the vapor phase with a catalyst which comprises a phosphorus vanadium mixed oxide, the atomic ratio of vanadium to phosphorus being in the range of about 0.5:1 to about 1.1:1 wherein the catalyst in the initial solid phase has a characteristic initial powder X-ray diffraction pattern, using copper K-alpha radiation as follows:

| | Line Position | |
|---|---|---|
| d angstrom | 2.θ | Intensity |
| 8.75 | 10.1 | 38 |
| 5.7 | 15.2 | 23 |
| 4.5 | 19.4 | 24 |
| 3.7 | 24.0 | 21 |
| 3.3 | 26.8 | 32 |
| 3.1 | 28.3 | 24 |
| 2.9 | 30.0 | 100 |

2. The process of claim 1 wherein the reaction temperature is about 650° to about 870° F.

3. The process of claim 1 wherein a fixed bed catalyst is used and the feedstock constitutes about 0.5 to about 1.7 mole percent butane.

4. A process for the manufacture of maleic anhydride which process comprises contacting a feedstock comprising n-butane and a gas containing molecular oxygen in the vapor phase with a catalyst which comprises a phosphorus vanadium divalent metal mixed oxide, the atomic ratio of vandium to phosphorous being in the range of about 0.5:1 to about 1.1:1 and the total atomic ratio of the metal to vanadium being in the range of about 0.001:1 to about 0.4:1 wherein the catalyst in the initial solid phase has a characteristic initial powder X-ray diffraction pattern using copper K-alpha radiation as follows:

| | Line Position | |
|---|---|---|
| d angstrom | 2.θ | Intensity |
| 8.75 | 10.1 | 38 |
| 5.7 | 15.2 | 23 |
| 4.5 | 19.4 | 24 |
| 3.7 | 24.0 | 21 |
| 3.3 | 26.8 | 32 |
| 3.1 | 28.3 | 24 |
| 2.9 | 30.0 | 100 |

5. The process of claim 4 wherein the reaction temperature is about 650° to about 870° F.

6. The process of claim 4 wherein a fixed-bed catalyst is used and the feedstock contains about 0.5 to about 1.7 mole percent butane.

7. A process for the manufacture of maleic anhydride which process comprises contacting a feedstock comprising n-butane and a gas containing molecular oxygen in the vapor phase with a catalyst which comprises a phosphorus vanadium zinc mixed oxide, the atomic ratio of vanadium to phosphorus being in the range of about 0.5:1 to about 1.1:1 and the total atomic ratio of zinc to vanadium being in the range of about 0.001:1 to about 0.4:1, wherein the catalyst in the initial solid phase has a characteristic powder X-ray diffraction pattern using copper K-alpha radiation as follows:

| | Line Position | |
|---|---|---|
| d angstrom | 2.θ | Intensity |
| 8.75 | 10.1 | 38 |
| 5.7 | 15.2 | 23 |
| 4.5 | 19.4 | 24 |
| 3.7 | 24.0 | 21 |
| 3.3 | 26.8 | 32 |
| 3.1 | 28.3 | 24 |
| 2.9 | 30.0 | 100 |

8. The process of claim 7 wherein the reaction temperature of about 650° to about 870° F.

9. The process of claim 7 wherein a fixed-bed catalyst is used and the feedstock contains about 0.5 to about 1.7 mole percent butane.

10. A process for the manufacture of maleic anhydride which process comprises contacting a feedstock comprising n-butane and a gas containing molecular oxygen in the vapor phase with a catalyst which comprises a phosphorus vanadium molybdenum mixed oxide, the atomic ratio of vanadium to phosphorus being in the range of about 0.5:1 to about 1.1:1 and the total atomic ratio of molybdenum to vanadium being in the range of about 0.001:1 to about 0.4:1, wherein the catalyst in the initial solid phase has a characteristic powder X-ray diffraction pattern using copper K-alpha radiation as follows:

| | Line Position | |
|---|---|---|
| d angstrom | 2.θ | Intensity |
| 8.75 | 10.1 | 38 |
| 5.7 | 15.2 | 23 |
| 4.5 | 19.4 | 24 |
| 3.7 | 24.0 | 21 |
| 3.3 | 26.8 | 32 |
| 3.1 | 28.3 | 24 |
| 2.9 | 30.0 | 100 |

11. The process of claim 10 wherein the reaction temperature is about 650° to about 870° F.

12. The process of claim 10 wherein a fixed-bed catalyst is used and the feedstock contains about 0.5 to about 1.7 mole percent butane.

* * * * *

UNITED STATES PATENT OFFICE
CERTIFICATE OF CORRECTION

Patent No. 4,482,726  Dated November 13, 1984

Inventor(s) CARL A. UDOVICH - WILLIAM S. ERYMAN

It is certified that error appears in the above-identified patent and that said Letters Patent are hereby corrected as shown below:

| Patent Column | Line | | |
|---|---|---|---|
| 2 | 50 | "VPMO Soluble $\xrightarrow{\Delta}_{N_2 \text{ vacuum}}$ VPMO solid" should be | -- VPMO Soluble $\xrightarrow{\Delta}$ $N_2$ vacuum solid -- |
| 1 | 62 | "2.0 degrees" should be | -- 2.θ degrees -- |
| 6 | 20 | "redbrown" should be | -- red-brown -- |
| 6 | 55 | "Flow 120 cc/MIN" | (should be moved up two lines) |
| 6 | 55 | "$P_2O_5/CH_3OH;Mo$" | (should be moved up two lines) |
| 6 | 62 | "Raised Temp. to 785°F." | (should be centered between and one space above "785" and "18.19") |
| 7 | 58 | "$P_2O_5/P_2O_5$ in syrup" | (should be moved up two lines) |
| 8 | 64 | "$p^{31}_{31}$" should be | -- $P^{31}_{31}$ -- |
| 9 | 7 | "$p^{31}$" should be | -- $P^{31}$ -- |

UNITED STATES PATENT OFFICE
CERTIFICATE OF CORRECTION

Patent No. 4,482,726  Dated November 13, 1984

Inventor(s) CARL A. UDOVICH - WILLIAM S. ERYMAN

It is certified that error appears in the above-identified patent and that said Letters Patent are hereby corrected as shown below:

| Patent Column | Line | | | |
|---|---|---|---|---|
| 10 | 33 | "of" | should be | -- at -- |
| 11 | 26 | "30.0" | should be | -- 30.3 -- |
| 11 | 56 | "30.0" | should be | -- 30.3 -- |
| 12 | 24 | "30.0 " | should be | -- 30.3 -- |
| 12 | 27 | "of" | should be | -- is -- |
| 12 | 52 | "30.0" | should be | -- 30.3 -- |

Signed and Sealed this

Seventeenth Day of September 1985

[SEAL]

Attest:

DONALD J. QUIGG

Attesting Officer

Commissioner of Patents and Trademarks—Designate